United States Patent [19]

Reuschling et al.

[11] 4,096,274
[45] Jun. 20, 1978

[54] PYRROLIDONES AND PROCESS FOR THEIR MANUFACTURE

[75] Inventors: Dieter-Bernd Reuschling, Butzbach; Klaus Kühlein, Kelkheim, Taunus; Adolf Linkies, Frankfurt am Main; Rudolf Kunstmann, Breckenheim, Taunus; Josef Musil, Konigstein, Taunus, all of Germany

[73] Assignee: Hoechst Aktiengesellschaft, Frankfurt am Main, Germany

[21] Appl. No.: 751,165

[22] Filed: Dec. 16, 1976

[30] Foreign Application Priority Data

Dec. 20, 1975 Germany .............................. 2557748

[51] Int. Cl.² .......................................... C07D 207/26
[52] U.S. Cl. ............................... 424/274; 260/326.45; 542/413; 542/426; 542/427; 542/429; 542/442
[58] Field of Search ...................... 260/240 R, 326.45; 424/74

[56] References Cited

U.S. PATENT DOCUMENTS

| 3,192,230 | 6/1965 | Lunsford et al. | 260/326.45 |
| 3,975,399 | 8/1976 | De Franco et al. | 260/326.2 |
| 4,012,429 | 3/1977 | Sakai et al. | 260/240 R |

OTHER PUBLICATIONS

Ambrus, et al., Chem. Abstracts, 84(1976), #59286.
Bruin, et al., Chem. Abstracts, 84(1976), #121582.
Rozing, et al., Chem. Abstracts, 85(1976), #20998.
Scribner, Chem. Abstracts, 80(1974), #47986.
Bolliger, et al., Tet. Letters, #34(1975), pp. 2931–2934.
Harrison, et al., Tet. Letters, #13(1975), pp. 1165–1168.

Primary Examiner—Arthur P. Demers
Attorney, Agent, or Firm—Curtis, Morris & Safford

[57] ABSTRACT

The present invention relates to novel pyrrolidone derivatives as well as to a process of preparing the same. The novel compounds have a pharmaceutical action similar to that of prostaglandins and can therefore be used as medicaments.

8 Claims, No Drawings

PYRROLIDONES AND PROCESS FOR THEIR MANUFACTURE

The natural prostaglandins have a carbon framework of generally 20 carbon atoms. They differ from one another in the number of hydroxyl groups and double bonds. As they exhibit a large number of physiological actions simultaneously and have only a short half-life period in the organism, their use as therapeutics is limited.

The search for prostaglandins having a longer half-life period and a specific action therefore becomes increasingly important.

The present invention is concerned with new pyrrolidones having a prostaglandin-like action of the formula

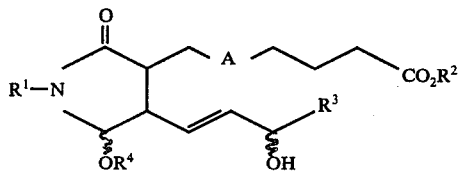

in which $R^1$ represents an α-branched alkyl residue containing 3 to 6 carbon atoms or a cycloalkyl residue containing 3 to 7 members in the ring, $R^2$ represents hydrogen, a low molecular weight aliphatic hydrocarbon residue or a cycloaliphatic or araliphatic hydrocarbon residue containing 3 to 8 carbon atoms, $R^3$ represents a straight chain or branched alkyl residue containing 1 to 10 carbon atoms, which may itself be substituted by an O-alkyl residue containing 1 to 5 carbon atoms, and/or by a phenyl residue or by a phenoxy residue, which two latter residues may be substituted by one or more optionally halogen substituted alkyl groups containing 1 to 3 carbon atoms and/or by one or more halogen atoms, or a cycloalkyl residue which may itself be substituted by one or more alkyl groups containing 1 to 3 carbon atoms, $R^4$ represents an alkyl residue containing 1 to 4 carbon atoms, A represents a —C≡C—, —CH=— (cis) or —CH$_2$—CH$_2$-group, and in which the side chains in the 3- and 4-position of the pyrrolidone ring are in the trans-position relatively to one another, and also the physiologically tolerable metal and amine salts of the free acids.

The subject of the invention is also a process for the manufacture of pyrrolidones of the general formula I, characterised in that (a) a compound of the general formula II

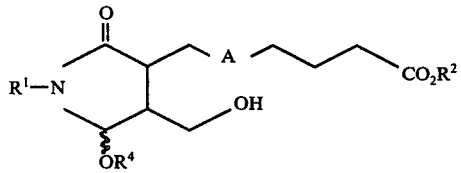

in which $R^1$, $R^2$, $R^4$ and A have the meanings given for formula I, provided that $R^2$ is not H, is oxidised to form an aldehyde of the formula III

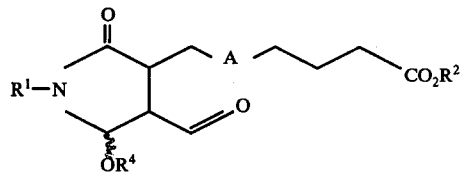

(b) the aldehyde of the formula III so obtained is reacted with a phosphonate of the formula IV

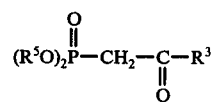

in which $R^3$ has the meaning given for formula I and $R^5$ represents a (C$_1$-C$_4$)-alkyl residue, to form a compound of the formula V

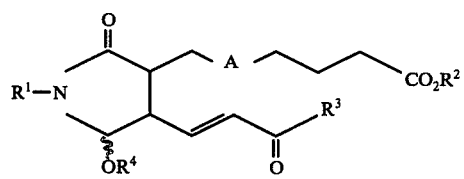

in which $R^1$, $R^2$, $R^3$, $R^4$ and A have the meanings given for formula I, provided that $R^2$ is not H, (c) in the compound of the formula V so obtained the ketocarbonyl group is reduced, whereby a compound of the formula I is formed, and the latter is optionally converted in the usual manner into the free acid or a physiologically tolerable metal or amine salt thereof.

The following substituents are preferred:

Among the meanings given for $R^1$, α-branched alkyl residues containing 3 to 4 carbon atoms, especially the isopropyl and also the tert.-butyl residue, and cycloalkyl residues contaning 5 to 6 members in the ring, especially the cyclohexyl residue;

among the meanings given for $R^2$, (C$_1$ - C$_4$)-alkyl residues, preferably the methyl residue, also cycloalkyl residues containing 5 to 7 carbon atoms, and aralkyl residues containing 7 to 8 carbon atoms, especially the benzyl residue; among the meanings given for $R^3$, alkyl residues containing 3 to 8 carbon atoms, cycloalkyl residues containing 5 to 7 carbon atoms, which may be substituted by the phenyl residue optionally being substituted by one to three methyl groups, further residues of the formula —C(R')$_2$—CH$_2$—O—R'', in which R' represents a (C$_1$ — C$_3$)-alkyl residue with the proviso that the two R's may be different, and in which R'' represents a (C$_1$ - C$_5$)-alkyl residue, a phenyl residue which may be substituted by 1 or 2 fluorine, chlorine and/or bromine atoms, by the trifluoromethyl residue or by one to three (C$_1$ - C$_3$)-alkyl residues.

For $R^4$ the methyl and ethyl group is preferred.

Especially preferred are, in addition to the residues for $R^3$ contained in the Examples: butyl, hexyl, heptyl, cyclohexyl and also residues of the formula

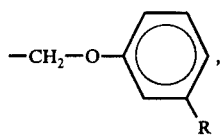

in which R = F, Cl, CF$_3$.

The pyrrolidones of the formula II used as starting materials in the process of the invention may be prepared as follows.

The compounds unsubstituted in the 5-position are first prepared in accordance with German Offenlegungsschrift No. 24 52 536. Then anodic alkoxylation in the 5-position is carried out, for example, in accordance with the simultaneously filed patent applicaton Ser. No. 751,335 filed Dec. 16, 1976.

In accordance with this process the compound unsubstituted in the 5-position is anodically alkoxylated with a lower alkanol in the presence of a conducting salt (see Example 1).

As alkanols there are suitable for carrying out the process of the invention: methanol, ethanol, n-propanol, isopropanol, n-butanol, sec.-butanol, etc. Methanol and ethanol, especially methanol, are preferred.

The conducting salts used for the process are the alkali (Li, Na, K, Rb, Cs) and also the tetra-alkylammonium salts of tetrafluoroboric acid, hexafluorophosphoric acid and nitric acid. The conducting salts may be used either alone or in admixture with one another. The alkyl residues present in the tetraalkylammonium group are those containing 1 to 6, and preferably 1 to 4, carbon atoms, especially the methyl and ethyl groups. The following conducting salts may be mentioned by way of example: Na-tetrafluoroborate, Na-nitrate, K-tetrafluoroborate, K-hexafluorophosphate, Rb-nitrate, tetramethylammonium-tetrafluoroborate, tetraethylammonium-tetrafluoroborate, tetra-n-butylammoniumtetrafluoroborate, tetraethylammonium-hexafluorophosphate, tetra-n-propylammonium-hexafluoroborate, tetra-n-butylammonium-hexafluoroborate, tetramethylammonium nitrate, etc. Preferred conducting salts are the alkali- and tetraalkylammonium-tetrafluoroborates, especially NaBF$_4$, KBF$_4$ and (CH$_3$)$_4$NBF$_4$.

The concentration of conducting salt in the electrolysis solution should be about 0.01 to about 2.0 mol per liter, and preferably about 0.02 to 1.0 mol per liter. An electrolysis temperature in the range of about $-10°$ to $+100°$ C, preferably about 0° to 60° C., has been preferred.

Molar ratios of starting compound to alcohol in the electrolysis solution in the range of about 1 : 1 to about 1 : 100 are possible; molar ratios of about 1 : 2 to about 1 : 60, and especially about 1 : 5 to about 1 : 50 are preferred.

The oxidation of the compounds of the formula II to form compounds of the formula III is carried out with oxidising agents that are customarily used for the oxidation of aliphatic alcohols to aldehydes, for example, by methods such as are described in Houben-Weyl, vol. 7/1, page 159. Further suitable oxidising agents are the complexes formed from thioethers such as dimethyl sulphide or thioanisole with chlorine or N-chloro-succinimide [E. J. Corey, C. U. Kim, J. Org. Chem. 38, 1233 (1973); E. J. Corey, C. U. Kim, J. Am. Chem. Soc. 94, 7586 (1972)]. Furthermore, the oxidation with dimethylsulphoxide can be carried out under a very wide variety of conditions [W. W. Epstein, F. W. Sweat, Chem. Rev. 67, 247 (1967)].

An especially preferred process is the oxidation with chromium trioxide-pyridine complex (J. C. Collins, Tetrahedron Letters 1968, 3363). The complex is first prepared in an inert solvent, preferably methylene chloride, and then a solution of the compound of formula II is added at $-10°$ C to $+10°$ C. The oxidation takes place rapidly and is usually terminated after 5 to 30 minutes.

The aldehyde of the formula III can be used without further purification for the next step of the process. If desired, the aldehyde is purified by column chromatography.

The reaction of the phosphates of the formula IV can be carried out with compounds of the formula III under the conditions customarily used for the Horner reaction, for example, in ethers at room temperature. As ethers there come into consideration preferably diethyl ether, tetrahydrofurane and dimethoxyethane. For better completion of the reaction the phosphate is used in excess. The reaction is usually complete after 1 to 5 hours at room temperature. The reaction product of the formula V is then isolated from the reaction mixture by the usual methods and purified by column chromatography.

The phosphates of the formula IV are either known [D. H. Wadsworth et al., J. Org. Chem. 30, 680 (1965)] or can be prepared in a manner analogous to the known methods.

Compounds of the formula I are obtained by the treatment of compounds of the formula V with a reducing agent. The reduction may be brought about with all reducing agents, which enable a keto group to be selectively reduced to a hydroxyl group. Preferred reducing agents are complex metal hydrides, especially the borohydrides such as sodium borohydride, zinc borohydride or lithium perhydro-9b-boraphenalkyl hydride [H. C. Brown, W. C. Dickason, J.Am.Chem.Soc. 92, 709 (1970)]. The reduction is usually carried out between 0° and 50° C in solvents that are inert towards the hydrides, such as diethyl ether, dimethyl-oxyethane, dioxane, tetrahydrofurane or diethylene glycol dimethyl ether. In a few cases it is of advantage to carry out the reduction by the Meerwein-Ponndorf-Verley method [J. Bowler and K. B. Mallion, Synthetic Commun. 4 (4), 211 (1974) and A. L. Wilds, "Reduction with Aluminium Alkoxides", Organic Reactions, Vol. 2, 178 (1944)], the isopropyl ester being formed simultaneously. The diastereomers formed in the reduction can be separated by means of the usual methods such as thick layer chromatography or column chromatography. Their conversion into the free acids is effected by one of the current methods of hydrolysis. The preparation of pharmacologically suitable salts from the acids is carried out in the usual manner. The acids are dissolved in a solvent such as water, methanol or tetrahydrofurane, neutralised with the appropriate organic or inorganic base and then, if the salt does not precipitate, a solvent of suitable polarity is added such as methanol, ethanol or dioxane, or evaporation to dryness is carried out.

Among the inorganic bases there are preferred the alkali and alkaline earth metal hydroxides. Among organic bases there come into consideration primary, secondary and tertiary amines such, for example, as methylamine, dimethylamine, trimethylamine, phenylethylamine, ethylenediamine, allylamine, piperidine, morpholine and pyrrolidone. There come into consideration also amines which contain hydrophilic groups such as ethanolamine and ephedrine. As quaternary bases there come into consideration, for example, tetramethyl- and benzyltrimethyl-ammonium hydroxide.

The esters of the formula I, the acids on which they are based and the salts which can easily be prepared therefrom exhibit prostaglandin-like actions. The new compounds have luteolytic, gastric juice secretion-inhibiting, bronchospasmolytic and/or antihypertensive properties. Furthermore, the new compounds of the invention are also useful and valuable intermediate products for the preparation of other substances having the action of prostaglandin.

For the various possible indications there come into consideration the following unit doses and daily doses:

Bronchodilatory action (as an aerosol):
  Unit dose : 0.1 - 1000 μg
  preferred: 1 - 200 μg (per shot of spray)
  Daily dose: 0.1 - 10 mg
Blood pressure lowering action
  Unit dose: 1 - 1000 μg
  preferred: 1 - 100 μg parenteral (i.v.)
  Daily dose: 1 - 10 mg
oral
  Unit dose: 0.5 - 1000 μg
  preferred: 1 - 500 μg oral
  Daily dose: 1mg - 10 mg The doses for use against gastro-intestinal disturbances correspond to those that are mentioned for use as blood pressure lowering agents.

The compounds of the general formulae III and V are valuable new intermediate products for the preparation of compounds of the formula I.

The following examples illustrate the invention.

EXAMPLE 1

1-Isopropyl-3-[6-carbomethoxy-2-hexin-yl(1)]-4-hydroxymethyl-5-methoxy-pyrrolidone.

In an electrolytic cell having a capacity of about 80 ml there are electrolysed 5.0 grams (15.5 mMol) of 1-isopropyl-3-[6-carbomethoxy-2-hexin-yl-(1)]-4-hydroxymethylpyrrolidone and 57.7 grams of methanol in the presence of 0.09 gram of tetramethylammonium-tetrafluoroborate as conducting salt. As electrodes there are immersed in the solution two concentrically arranged platinum cylinders having 225 meshes per square centimeter having diameters of 15 and 30 mm and a height of 50 mm. The outer electrode is connected as anode. The temperature is maintained at about 10° C. during the hydrolysis. After switching on the electrolytic direct current the anode current density is 1 A/dm². After the passage of a quantity of current of 2.44 Faraday equivalents per mol of starting pyrrolidone the current is switched off. The calculated mean cell voltage is 31.2 volts. For working up, the methanol is distilled off in vacuo and the residue is purified by column chromatography (silica gel/ethyl acetate). 3.35 grams (60.8%) of the above mentioned compound are obtained.

The cis/trans ratio of the substituents in the 4- and 5-position is about 1:1.

$R_{F1}$ = 0.61; $R_{F2}$ = 0.55 (ethyl acetate)
NMR (CDCl$_3$): δ = CO$_2$CH$_3$ 3.63,

4.13,

1.24 N—CH—O 4.77 (trans), N—CH—O 4.89 (cis), C—O—CH$_3$ 3.31 (trans), C—O—CH$_3$ 3.49 (cis) ppm.

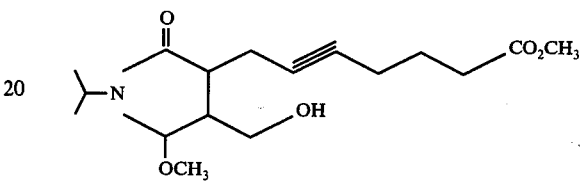

EXAMPLE 2

1-Isopropyl-3-[6-carbomethoxy-2-hexin-yl-(1)]-4-[3-oxo-(E)-1-octen-yl-(1)]-5-methoxy-pyrrolidone.

(a) Into a stirred solution of 13.2 grams (166 mmol) of pyridine in 200 ml of absolute methylene chloride are introduced in portions at room temperature 8.3 grams (83 mmol) of chromium trioxide. The mixture is further stirred for 20 minutes at room temperature, cooled to 0° C., and a solution of 10 mmol of 1-isopropyl-3-[6-carbomethoxy-2-hexin-yl-(1)-]-4-hydroxy-methyl-5-methoxypyrrolidone in 25 ml of absolute methylene chloride is added dropwise in the course of 10 minutes. After a further 30 minutes, 75 ml of 2N-sulphuric acid are added, the organic phase is separated off, dried and evaporated in vacuo at a bath temperature of which the maximum is 30° C. The 1-isopropyl-3-[6-carbomethoxy-2-hexin-yl-(1)]-4-formyl-5-methoxy-pyrrolidone [$R_{F1}$ = 0.65, $R_{F2}$ = 0.77 (ethyl acetate)] so obtained is used without further purification for the next reaction stage.

(b) 10 mmol of dimethyl-(2-oxoheptyl)-phosphonate are introduced into 25 ml of absolute dimethoxyethane and at −70° C. 10 mmol of lithium butyl in hexane are added. After stirring for 15 minutes, the crude aldehyde from Example (2a), dissolved in 15 ml of absolute dimethoxyethane, is added dropwise at −70° C. The mixture is then further stirred for 10 minutes at −70° C. and 60 minutes at room temperature. The mixture is then adjusted to a pH value of 3 - 5 at 0° C. with 2N-sulphuric acid. The organic solvent is distilled off in vacuo at room temperature to a great extent. To the residue are added diethyl ether and 30 ml of water. The organic phase is separated, and the aqueous phase is extracted several times with diethyl ether. By drying and evaporating the total ether phases, there is obtained crude 1-isopropyl-3-[6-carbomethoxy-2-hexin-yl-(1)]-4-[3-oxo-(E)-1-octenyl-(1)]-5-methoxy-pyrrolidone, which is purified by column chromatography (silica gel/diethyl ether). $R_F$ = 0.81 (diethyl ether)

IR (CH$_2$Cl$_2$): ν = 1745 (C═O), 1705 (C═O), 1645 (C═C) cm$^{-1}$ NMR (CDCl$_3$): δ = CO$_2$CH$_3$ 3.63,

4.09

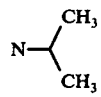

1.23,

N—CH—
|
O 4.67 and 4.79

O—CH₃ 3.30 and 3.32, C—CH₃ 0.88 olefin 6.18 – 6.98 ppm.

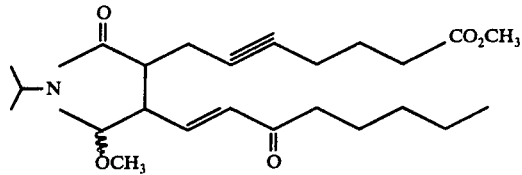

EXAMPLE 3

1-Isopropyl-3-[6-carbomethoxy-2-hexin-yl-(1)]-4-[3-oxo-4,4-dimethyl-(E)-1-octen-yl-(1)]-5-methoxy-pyrrolidone is obtained in a manner analogous to that in Example (2a, b) by the use of dimethyl-(2-oxo-3,3-dimethyl-heptyl)phosphonate. $R_F$ = 0.79 (diethyl ether)
IR ($CH_2Cl_2$): $\nu$ = 1740 (C=O), 1700 (C=O), 1640 (C=C) cm$^{-1}$

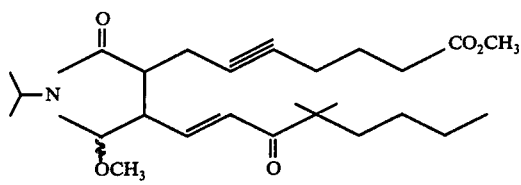

EXAMPLE 4

1-Isopropyl-3-[6-carbomethoxy-2-hexin-yl-(1)]-4-[3-oxo-4,4-dimethyl-5-ethoxy-(E)-1-penten-yl-(1)]-5-methoxy-pyrrolidone is obtained in a manner analogous to that in Example (2a, b) by the use of dimethyl-(2-oxo-3,3-dimethyl)-4-ethoxy-butyl)phosphonate.

$R_F$ = 0.70 (diethyl ether)
IR ($CH_2Cl_2$): $\nu$ = 1740 (C=O), 1700 (C=O), 1640 C=C) cm$^{-1}$

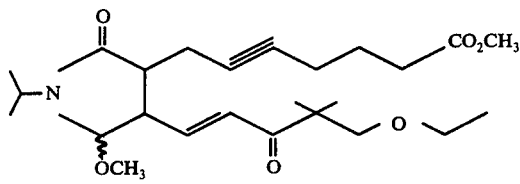

EXAMPLE 5

1-Isopropyl-3-[6-carbomethoxy-2-hexin-yl-(1)]-4-[3-oxo-4-phenyl-4ethoxy-(E)-1-buten-yl-(1)]-5-methoxy-pyrrolidone is obtained in a manner analogous to that in Example (2a, b) by using dimethyl-(2-oxo-3-phenyl-3-ethoxy-propyl)-phosphonate.

$R_F$ = 0.71 (diethyl ether)
IR ($CH_2Cl_2$): $\nu$ = 1740 (C=O), 1685 (C=O), 1640 C=C) cm$^{-1}$

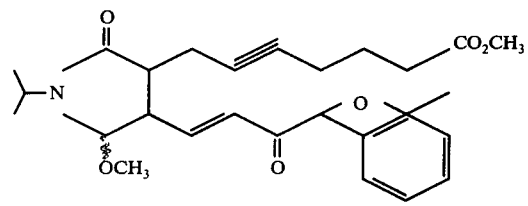

EXAMPLE 6

1-Isopropyl-3-[6-carbomethoxy-2-hexin-yl-(1)]-4-[3-oxo-3-cyclohexyl-(E)-1-propen-yl-(1)]-5-methoxy-pyrrolidone is obtained in a manner analogous to that in Example (2a, b) by the use of dimethyl-(2-oxo-2-cyclohexyl-ethyl)-phosphonate.

$R_F$ = 0.70 (diethyl ether)
IR ($CH_2Cl_2$): $\nu$ = 1740 (C=O), 1700 (C=O), 1640 (C=C) cm$^{-1}$

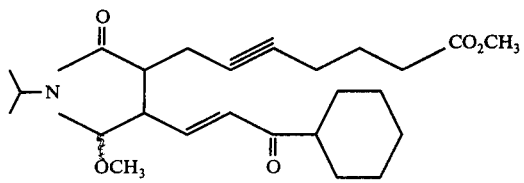

EXAMPLE 7

1-Isopropyl-3-[6-carbomethoxy-2-hexin-yl-(1)]-4-[3-(RS)hydroxy-(E)-1-octen-yl-(1)]-5-methoxy-pyrrolidone.

To a solution of 1.0 gram (2.4 mmol) of 1-isopropyl-3-[6-carbomethoxy-2-hexin-yl-(1)]-4-[3-oxo-(E)-1-octen-yl(1)]-5-methoxy-pyrrolidone (obtained in accordance with Example 2) in 25 ml of absolute dimethoxyethane are added dropwise at 0° C 15 ml of an 0.84 molar Zn(BH₄)₂-solution (12.5 mmol), and the whole is stirred for 2.5 hours at room temperature. 2N-sulphuric acid is added ($p_H$ = 5), stirring is carried out for a short time and then the mixture is buffered with a saturated solution of sodium bicarbonate to a $p_H$ value of 7. The filtered solution is evaporated in vacuo, and the residue is extracted three times with 100 ml of methylene chloride each time. The organic phase is dried and evaporated in vacuo. The oil that remains behind is purified by column chromatography (silica gel; diethyl ether). $R_{F1}$ = 0.39, $R_{F2}$ = 0.45 (diethyl ether)

IR ($CH_2Cl_2$): $\nu$ = 3350 – 3500 (OH), 1735 (C=O), 1695 (C=O) cm$^{-1}$

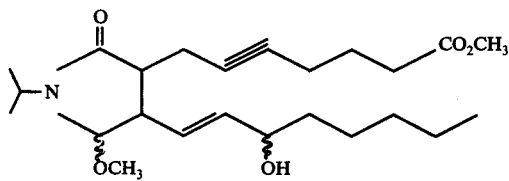

EXAMPLE 8

1-Isopropyl-3-[6-carbomethoxy-(Z)-2-hexen-yl-(1)]-4-[3-(RS)hydroxy-(E)-1-octen-yl-(1)]-5-methoxy-pyrrolidone 1-Isopropyl-3-[6-carbomethoxy-(Z)-2-hexen-yl-(1)]-4-hydroxymethyl-pyrrolidone, obtained in accordance with Patent Applications P 24 52 536.8 and P 25 28 036.8, is converted in a manner analogous to that in Example (1) by electrochemical methoxylation into 1-isopropyl-3-[6-carbomethoxy-(Z)-2-hexenyl-(1)]-4-hydroxymethyl-5-methoxy-pyrrolidone and the latter is reacted in accordance with Example (2a, b) to form the corresponding -4-[3-oxo-(E)-1-octen-yl-(1)]-compound. By reduction in accordance with Example (7) there is obtained 1-isopropyl-3-[6-carbomethoxy-(Z)-2-hexen-yl-(1)]-4-[3-(RS)hydroxy-(E)-1-octen-yl-(1)]-5-methoxy-pyrrolidone.

$R_{F1} = 0.55$, $R_{F2} = 0.61$ (diethyl ether)

IR (CH$_2$Cl$_2$): $\nu$ = 3350 – 3550 (OH), 1745 (C=O), 1700 (C=O) cm$^{-1}$

NMR (CDCl$_3$): $\delta$ = CO$_2$CH$_3$ 3.62,

4.12

1.21, N—CH—O 4.52 and 4.64, OCH$_3$ 3.29, C—CH$_3$ 0.89, olefin 5.30 – 5.70 ppm

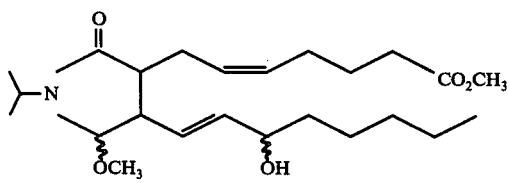

EXAMPLE 9

1-Isopropyl-3-[6-carbomethoxy-2-hexin-yl-(1)]-4-[3-(RS)hydroxy-4,4-dimethyl-5-ethoxy-(E)-1-penten-yl(1)]-5-methoxypyrrolidone is obtained in a manner analogous to that in Example (7) from 1-isopropyl-3-[6-carbomethoxy-2-hexin-yl-(1)]-4-[3-oxo-4,4-dimethyl-5-ethoxy-(E)-1-penten-yl-(1)]-5-methoxypyrrolidone (obtained according to Example 4).

$R_F = 0.55$ (diethyl ether)

IR (CH$_2$Cl$_2$): $\nu$ = 3480 (OH), 1740 (C=O), 1700 (C=O) cm$^{-1}$

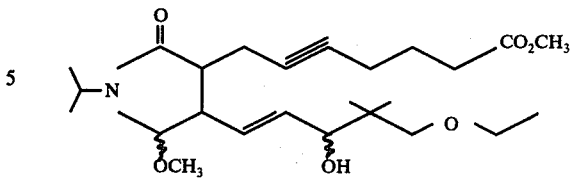

EXAMPLE 10

1-Isopropyl-3-[6-carboisopropyloxy-2-hexin-yl(1)]-4-[3-(RS)hydroxy-4-phenyl-4-ethoxy-(E)-1-buten-yl-(1)]-5-methoxypyrrolidone.

5 mmol of 1-isopropyl-3-[6-carbomethoxy-2-hexin-yl(1)]-4-[3-oxo-4-phenyl-4-ethoxy-(E)-1-buten-yl(1)]-5-methoxy-pyrrolidone (obtained in accordance with Example 5) are boiled under reflux together with 25 mmol of freshly distilled aluminium triisopropylate in 25 ml of absolute toluene for 2 to 3 hours. After cooling, the mixture is adjusted to a $p_H$ value of 2 – 3 with 1N-sulphuric acid with further cooling, the organic phase is separated and the aqueous phase extracted several times with methylene chloride. The combined organic phases are dried over sodium sulphate and evaporated in vacuo. For purification, the reaction product is chromatographed over silica gel (diethyl ether).

$R_{F1} = 0.60$, $R_F^2 = 0.66$ (diethyl ether),

IR (CH$_2$Cl$_2$): $\nu$ = 3350 – 3500 (OH), 1720 (C=O), 1685 (C=O) cm$^{-1}$

NMR (CDCl$_3$):

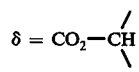

4.98,

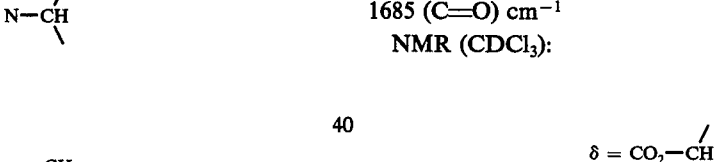

1.21,

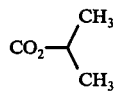

4.10,

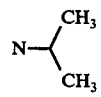

1.21, N—CH—O 4.46 and 4.63, OCH$_3$ 3.25, phenyl 7.27 olefin 5.30–5.70 ppm.

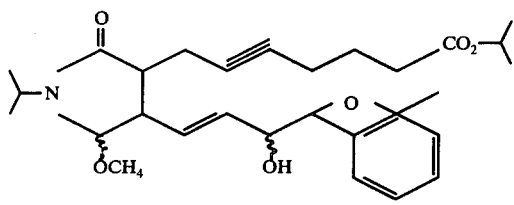

EXAMPLE 11

1-Isopropyl-3-[6-carboisopropyloxy-2-hexin-yl-(1)]-4-[3-(RS)hydroxy-3-cyclohexyl-(E)-1-propen-yl-(1)]-5-methoxy-pyrrolidone is obtained in a manner analogous to that in Example (10) from 1-isopropyl-3-[6-carbomethoxy-2-hexin-yl-(1)]-4-[3-oxo-3-cyclohexyl-(E)-1-propen-yl(1)]-5-methoxy-pyrrolidone (obtained in accordance with Example 6).

$R_{f1} = 0.63$, $R_{f2} = 0.68$ (diethyl ether).
IR ($CH_2Cl_2$): $\nu$ = 3450 (OH), 1725 (C=O), 1690 (C=O) cm$^{-1}$.
NMR ($CDCl_3$):

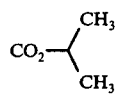

4.99,

1.21,

4.10

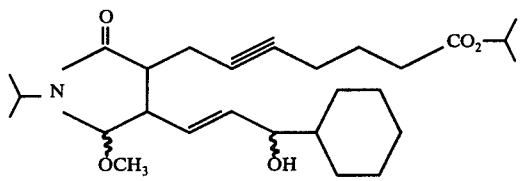（note: "N—" structure with CH3/CH3）

1.21, N—CH—O 4.58 and 4.72, OCH$_3$ 3.33, olefin 5.50 – 5.80 ppm.

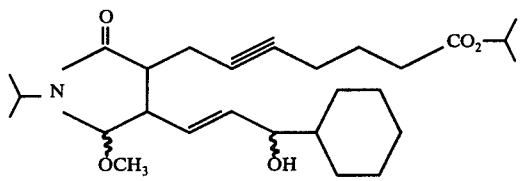

EXAMPLE 12

1-Isopropyl-3-[6-carboisopropyloxy-2-hexin-yl-(1)]-4-[3-(RS)hydroxy-4,4-dimethyl-(E)-1-octen-yl-(1)]-5-methoxy-pyrrolidone is obtained in a manner analogous to that in Example (10) from 1-isopropyl-3-[6-carbomethoxy-2-hexin-yl-(1)]-4-[3-oxo-4,4-dimethyl-(E)-1-octen-yl-(1)]-5-methoxy-pyrrolidone (obtained in accordance with Example 3).

$R_{f1} = 0.55$, $R_{f2} = 0.62$ (diethyl ether).
IR ($CH_2Cl_2$): $\nu$ = 3300 – 3500 (OH), 1720 (C=O), 1685 (C=O) cm$^{-1}$.
NMR ($CDCl_3$):

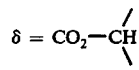

5.00,

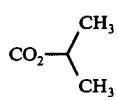

1.23,

4.10

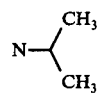

1.23 N—CH—O 4.58 and 4.72, OCH$_3$ 3.34,

1.26, C—CH$_3$ 0.90, olefin 5.60 – 5.80 ppm.

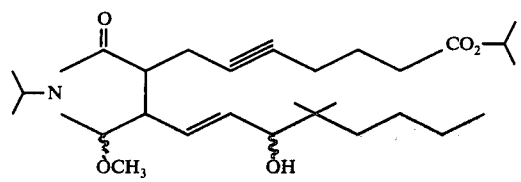

EXAMPLE 13

1-Isopropyl-3-[6-carboisopropyloxy-(Z)-2-hexen-yl-(1)]-4-[3(RS)-hydroxy-4,4-dimethyl-(E)-1-octen-yl-(1)]-5-methoxypyrrolidone is obtained, starting from 1-isopropyl-3-[6-carbomethoxy-(Z)-2-hexen-yl-(1)]-4-hydroxymethyl-pyrrolidone, with the use of the process stages analogous to Examples (1) and (3) from 1-isopropyl-3-[6-carbomethoxy-(Z)-2-hexen-yl-(1)]-4-[3-oxo-4,4-dimethyl-(E)-1-octen-yl-(1)]-5-methoxy-pyrrolidone in a manner analogous to Example (10).

$R_{f1} = 0.59$, $R_{f}^2 = 0.66$ (diethyl ether).
IR ($CH_2Cl_2$): $\nu$ = 3350 – 3500 (OH), 1740 (C=O), 1795 (C=O) cm$^{-1}$.

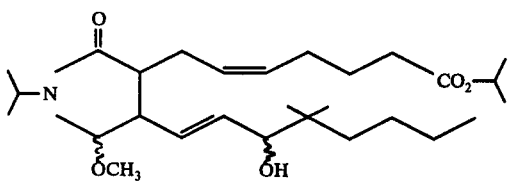

EXAMPLE 14

1-Isopropyl-3-[6-carbomethoxy-(Z)-2-hexen-yl-(1)]-4-[3-(RS)-hydroxy-4,4-dimethyl-ethoxy-(E)-1-pentenyl-(1)]-5-methoxypyrrolidone is obtained in a manner analogous to that in Example (7) from 1-isopropyl-3-[6-carbomethoxy-(Z)-2-hexen-yl-(1)]-4-[3-oxo-4,4-dimethyl-5-ethoxy-(E)-1-penten-yl-(1)]-5-methoxypyrrolidone (obtainable from 1-isopropyl-3-[6-carbomethoxy(Z)-2-hexen-yl-(1)]-4-hydroxymethyl-pyrrolidone in a manner analogous to that in Example 1 and Example 4).

$R_F$ = 0.71 (diethyl ether).

IR ($CH_2Cl_2$): $\nu$ = 3500 (OH), 1740 (C=O), 1700 (C=O) $cm^{-1}$.

NMR ($CDCl_3$): $\delta$ $CO_2CH_3$ 3.61,

4.11,

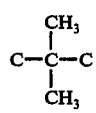

1.21, N—CH—O 4.54 and 4.64, $OCH_3$ 3.29

$$C-\underset{\underset{CH_3}{|}}{\overset{\overset{CH_3}{|}}{C}}-C$$

0.86, O—$CH_2$—C 3.45, O—C—$CH_3$ 1.18 olefin 5.30–5.80 ppm

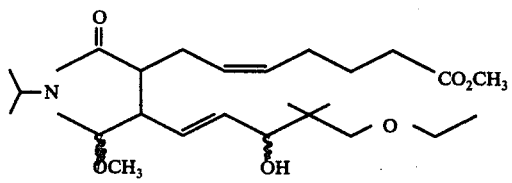

EXAMPLE 15

1-Isopropyl-3-[6-carbomethoxy-(Z)-2-hexen-yl-(1)]-4-[3-(RS)-hydroxy-4-phenyl-4-ethoxy-(E)-1-buten-yl-(1)]-5-methoxypyrrolidone is obtained, starting from 1-isopropyl-3-[6-carbomethoxy-(Z)-2-hexen-yl-(1)]-4-hydroxymethyl-pyrrolidone with the use of process stages analogous to Examples (1) and (5), from 1-isopropyl-3-[6-carboymethoxy-(Z)-2-hexen-yl-(1)]-4-[3-oxo-4-phenyl-4-ethoxy-(E)-1-buten-yl-(1)]-5-methoxy-pyrrolidone in a manner analogous to that in Example (10).

$R_{F1}$ = 0.58, $R_{F2}$ = 0.64 (diethyl ether).

IR ($CH_2Cl_2$): $\nu$ = 3350 - 3550 (OH), 1725 (C=O), 1690 (C=O). NMR ($CDCl_3$):

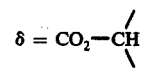

5.00

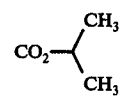

1.21,

4.10,

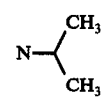

1.21, $OCH_3$ 3.22, N—CH—O 4.39 and 4.56, phenyl 7.27, olefin 5.15 – 5.70 ppm.

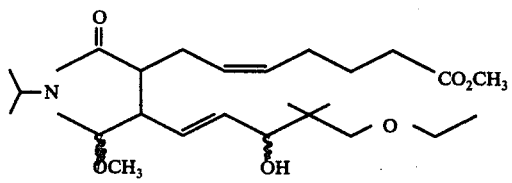

EXAMPLE 16

1-Isopropyl-3-[6-carboisopropyloxy-(Z)-2-hexen-yl-(1)]-4-[3-(RS)-hydroxy-3-cyclohexyl-(E)-1-propen-yl-(1)]-5-methoxypyrrolidone is obtained starting from 1-isopropyl-3-[6-carbomethoxy-(Z)-2-hexen-yl-(1)]-4-hydroxymethyl-pyrrolidone with the use of the process stages analogous to Examples (1) and (6) from 1-isopropyl-3-[6-carbomethoxy-(Z)-2-hexen-yl-(1)]-4-[3-oxo-3-cyclohexyl-(E)-1-propen-yl-(1)]-5-methoxy-pyrrolidone in a manner analogous to that in Example (10).

$R_{F1}$ = 0.63, $R_{F2}$ = 0.72 (diethyl ether).

IR ($CH_2Cl_2$): $\nu$ = 3300 - 3500 (OH), 1725 (C=O), 1695 (C=O)

NMR ($CDCl_3$):

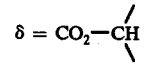

4.99,

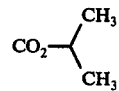

1.22,

4.12,

1.22, N—CH—O 4.53 and 4.65, OCH₃ 3.31, olefin 5.30 – 5.80 ppm.

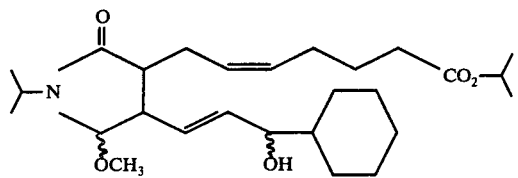

EXAMPLE 17

1-Isopropyl-3-[6-carbohydroxy-(Z)-2-hexen-yl-(1)]-4-[3-(RS)-hydroxy-(E)-1-octen-yl-(1)]-5-methoxy-pyrrolidone.

1.5 mmol of 1-isopropyl-3-[6-carbomethoxy-(Z)-2-hexen-yl-(1)]-4-[3-(RS)-hydroxy-(E)-1-octen-yl-(1)]-5-methoxy-pyrrolidone, obtained in accordance with Example (8), are dissolved in a mixture of 25 ml of a 1N-solution of sodium hydroxide, 5 ml of methanol and 5 ml of dimethoxyethane, and the mixture is stirred for 5 hours at room temperature. The mixture is acidified with 1N-sulphuric acid ($p_H$ = 3) and extracted several times with methylene chloride, and the organic phase is dried over sodium sulphate and evaporated. As a residue is obtained the desired compound in the form of a colorless viscous oil.

$R_F$ = 0.32 (HCCl₃ : CH₃OH = 90 : 10)

IR (CH₂Cl₂): $\nu$ = 3200 – 3450 (OH), 1720 (C=O), 1690 (C=O) cm⁻¹.

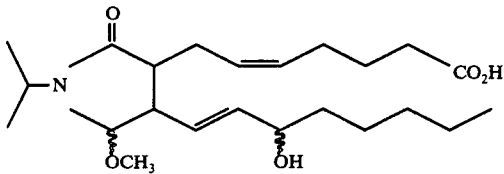

EXAMPLE 18

1Isopropyl-3-[6-carbohydroxy-2-hexin-yl-(1)]-4-[3-(RS)-hydroxy-(E)-1-octen-yl-(1)]-5-methoxy-pyrrolidone is obtained in a manner analogous to that in Example (17) from 1-isopropyl-3-[6-carbomethoxy-2-hexin-yl-(1)]-4-[3-(RS)-hydroxy-(E)-1-octen-yl-(1)]-5-methoxy-pyrrolidone (obtained in accordance with Example 7).

$R_F$ = 0.31 (HCCl₃ : CH₃OH = 90 : 10)

IR (CH₂Cl₂): $\nu$ = 3200–3500 (OH), 1720 (C=O), 1695 (C=O) cm⁻¹

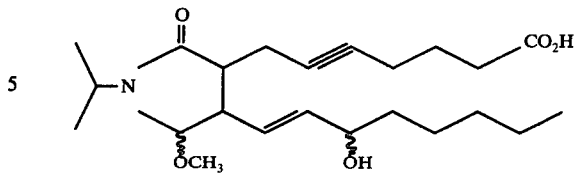

By the same process there can be prepared especially also the following compounds of the formula I, and in this manner not only the esters mentioned, but obviously also the corresponding acids and physiologically tolerable amine and metal salts thereof are obtainable:

(19) 1-Isopropyl-3-[6-carbomethoxy-2-hexin-yl-(1)]-4-[3-(RS)-hydroxy-(E)-1-hepten-yl-(1)]-5-methoxy-pyrrolidone

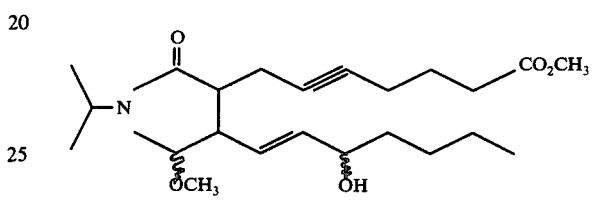

(20) 1-Isopropyl-3-[6-carbomethoxy-(Z)-2-hexen-yl-(1)]-4-[3-(RS)-hydroxy-(E)-1-hepten-yl-(1)]-5-methoxy-pyrrolidone

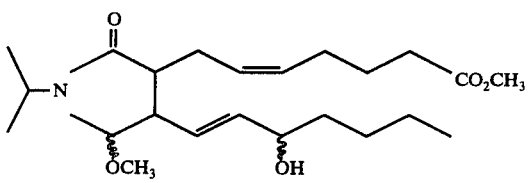

(21) 1-Isopropyl-3-[6-carbomethoxy-hexenyl-(1)]-4-[3-(RS)-hydroxy-(E)-1-hepten-yl-(1)]-5-methoxy-pyrrolidone

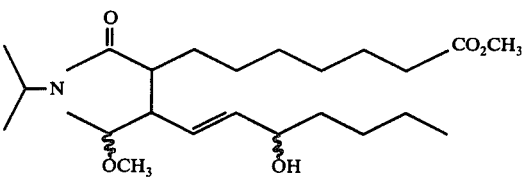

(22) 1-Isopropyl-3-[6-carbomethoxy-2-hexin-yl-(1)]-4-[3-(RS)-hydroxy-(E)-1-nonen-yl-(1)]-5-methoxy-pyrrolidone

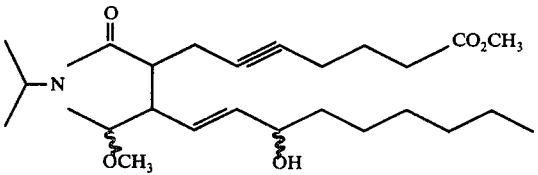

(23) 1-Isopropyl-3-[6-carbomethoxy-(Z)-2-hexen-yl-(1)]-4-[3-(RS)-hydroxy-(E)-1-nonen-yl-(1)]-5-methoxy-pyrrolidone

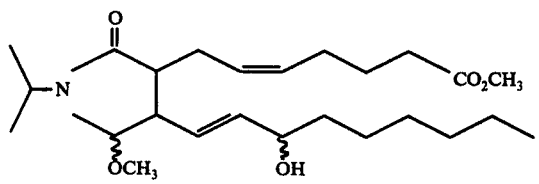

(24) 1-Isopropyl-3-[6-carbomethoxy-hexanyl-(1)]-4-[3-(RS)-hydroxy-(E)-1-nonen-yl-(1)]-5-methoxy-pyrrolidone

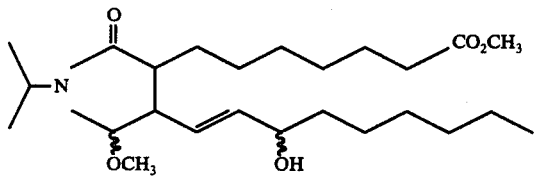

(25) 1-Isopropyl-3-[6-carbomethoxy-2-hexin-yl-(1)]-4-[3-(RS)-hydroxy-(E)-1-decen-yl-(1)]-5-methoxy-pyrrolidone

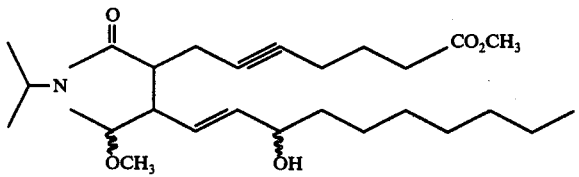

(26) 1-Isopropyl-3-[6-carbomethoxy-(Z)-2-hexen-yl-(1)]-4-[3-(RS)-hydroxy-(E)-1-decen-yl-(1)]-5-methoxy-pyrrolidone

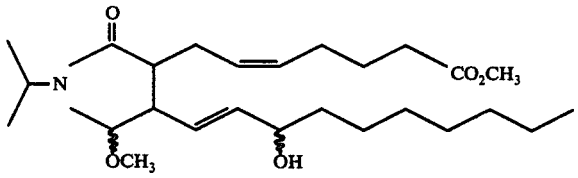

(27) 1-Isopropyl-3-[6-carbomethoxy-hexanyl-(1)]-4-[3-(RS)-hydroxy-(E)-1-decen-yl-(1)]-5-methoxy-pyrrolidone

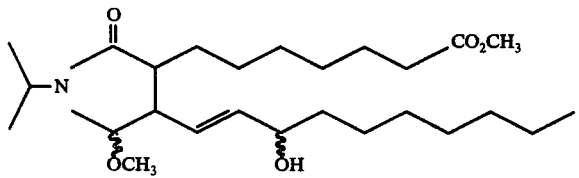

(28) 1-Isopropyl-3-[6-carbomethoxy-2-hexin-yl-(1)]-4-[3-(RS)-hydroxy-3-cycloheptyl-(E)-1-propen-yl-(1)]-5-methoxy-pyrrolidone

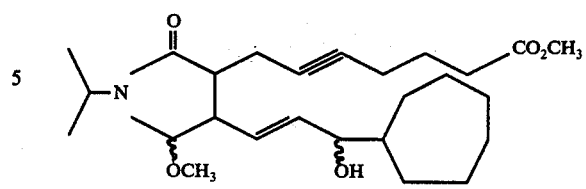

(29) 1-Isopropyl-3-[6-carbomethoxy-(Z)-2-hexen-yl-(1)]-4-[3-(RS)-hydroxy-3-cycloheptyl-(E)-1-propen-yl]-5-methoxy-pyrrolidone

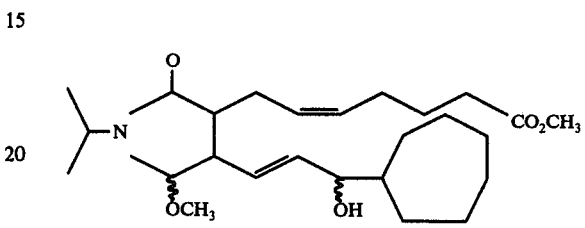

(30) 1-Isopropyl-3-[6-carbomethoxy-hexanyl-(1)]-4-[3-(RS)-hydroxy-3-cycloheptyl-(E)-1-propen-yl-(1)]-5-methoxy-pyrrolidone

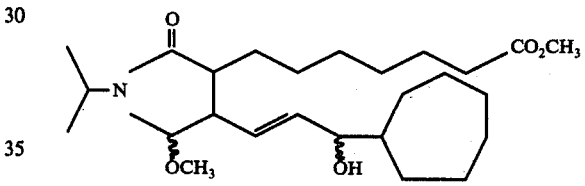

(31) 1-Isopropyl-3-[6-carbomethoxy-2-hexin-yl-(1)]-4-[3-(RS)-hydroxy-4-(4-chlorophenoxy)-(E)-1-buten-yl-(1)]-5-methoxy-pyrrolidone

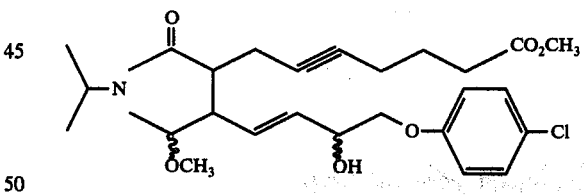

(32) 1-Isopropyl-3-[6-carbomethoxy-(Z)-2-hexen-yl-(1)]-4-[3-(RS)-hydroxy-4-(4-chlorophenoxy)-(E)-1-buten-yl-(1)]-5-methoxy-pyrrolidone

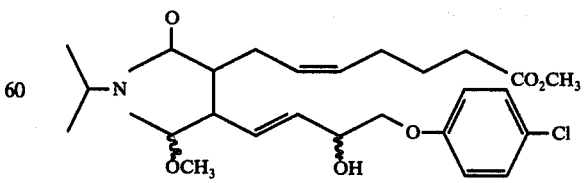

(33) 1-Isopropyl-3-[6-carbomethoxy-hexanyl-(1)]-4-[3-(RS)-hydroxy-4-(4-chlorophenoxy)-(E)-1-buten-yl-(1)]-5-methoxy-pyrrolidone

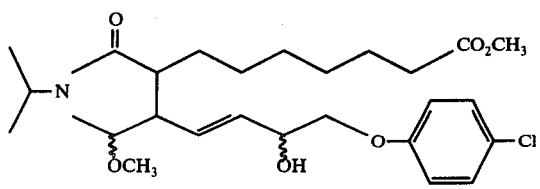

(34) 1-Isopropyl-3-[6-carbomethoxy-2-hexin-yl-(1)]-4-[3-(RS)-hydroxy-4-(4-fluorophenoxy)-(E)-1-buten-yl-(1)]-5-methoxy-pyrrolidone

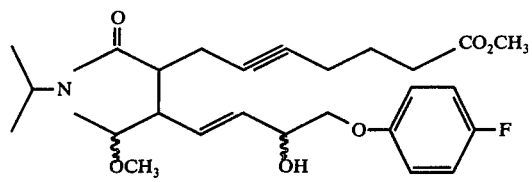

(35) 1-Isopropyl-3-[6-carbomethoxy-(Z)-2-hexen-yl-(1)]-4-[3-(RS)-hydroxy-4-(4-fluorophenoxy)-(E)-1-buten-yl-(1)]-5-methoxy-pyrrolidone

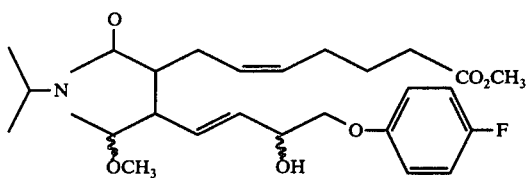

(36) 1-Isopropyl-3-[6-carbomethoxy-hexanyl-(1)]-4-[3-(RS)-hydroxy-4-(4-fluorophenoxy)-(E)-1-buten-yl-(1)]-5-methoxy-pyrrolidone

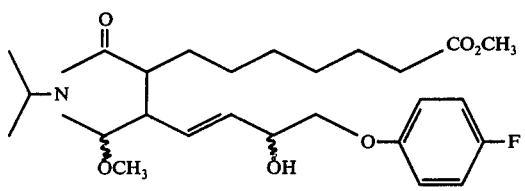

(37) 1-Isopropyl-3-[6-carbomethoxy-2-hexin-yl-(1)]-4-[3-(RS)-hydroxy-4-(3-chlorophenoxy)-(E)-1-buten-yl-(1)]-5-methoxy-pyrrolidone

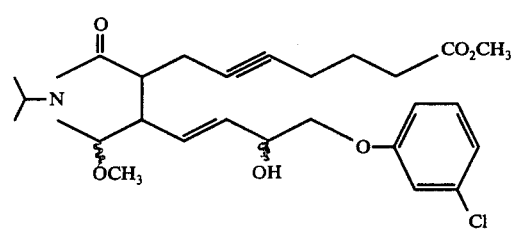

(38) 1-Isopropyl-3-[6-carbomethoxy-(Z)-2-hexen-yl-(1)]-4-[3-(RS)-hydroxy-4-(3-chlorophenoxy)-(E)-1-buten-yl-(1)]-5-methoxy-pyrrolidone

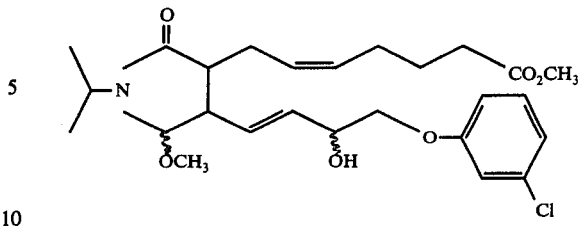

(39) 1-Isopropyl-3-[6-carbomethoxy-hexanyl-(1)]-4-[3-(RS)-hydroxy-4-(3-chlorophenoxy)-(E)-1-buten-yl-(1)]-5-methoxy-pyrrolidone

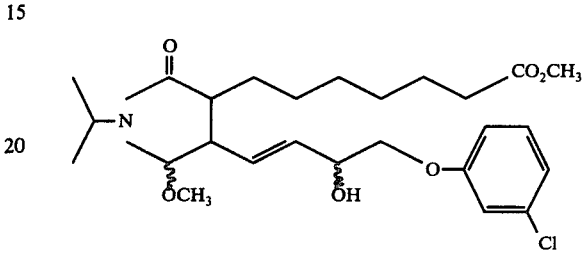

(40) 1-Isopropyl-3-[6-carbomethoxy-2-hexin-yl-(1)]-4-[3-(RS)-hydroxy-4-(3-trifluoromethylphenoxy)-(E)-1-buten-yl-(1)]-5-methoxy-pyrrolidone

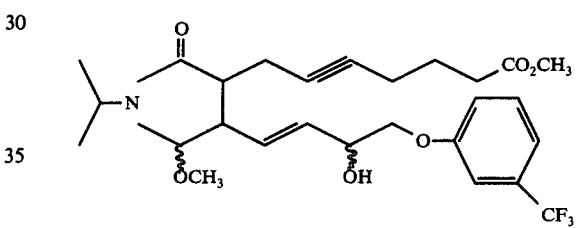

(41) 1-Isopropyl-3-[6-carbomethoxy-(Z)-2-hexen-yl-(1)]-4-[3-(RS)-hydroxy-4-(3-trifluoromethylphenoxy)-(E)-1-buten-yl-(1)]-5-methoxy-pyrrolidone

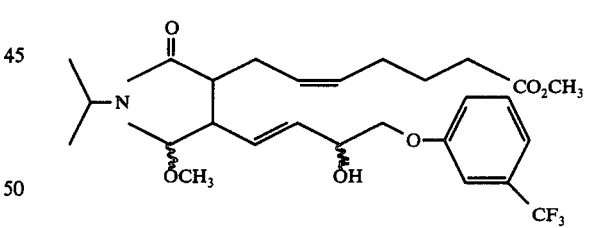

(42) 1-Isopropyl-3-[6-carbomethoxy-hexanyl-(1)]-4-[3-(RS)-hydroxy-4-(3-trifluoromethylphenoxy)-(E)-1-buten-yl-(1)]-5-methoxy-pyrrolidone

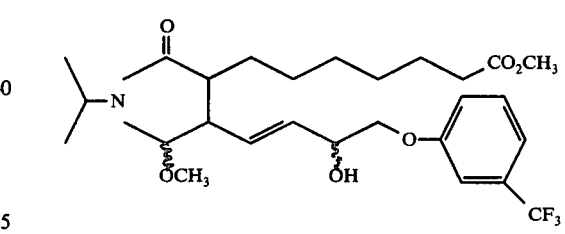

We claim:

1. A compound of the formula

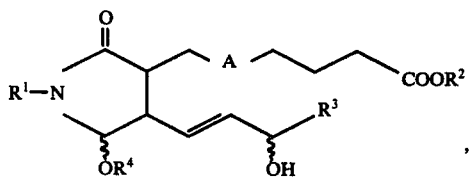

or a physiologically tolerable metal or amine salt of the free acid form thereof, wherein $R^1$ is α-branched alkyl having 3 to 6 carbon atoms or cycloalkyl having 3 to 7 carbon atoms in the ring;

$R^2$ is hydrogen, lower alkyl, or cycloalkyl or aralkyl having 3 to 8 carbon atoms;

$R^3$ is straight-chain or branched alkyl having 1 to 10 carbon atoms, or such alkyl substituted by O-alkyl havng 1 to 5 carbon atoms, by phenyl, by phenoxy, by cycloalkyl, by cycloalkyl in turn substituted by alkyl having 1 to 3 carbon atoms, or phenyl or phenoxy each in turn substituted by halogen, alkyl having 1 to 3 carbon atoms, or haloalkyl having 1 to 3 carbon atoms;

$R^4$ is alkyl having 1 to 4 carbon atoms; and

A is —C≡C—, —CH═CH—(cis), or —CH$_2$—CH$_2$—, in which compound or salt the chains in the 3- and 4- positions of the pyrrolidone ring are in transposition with respect to each other.

2. The method of making a compound as in claim 1 wherein $R^2$ is other than hydrogen which method comprises (a) oxidizing a compound of the formula

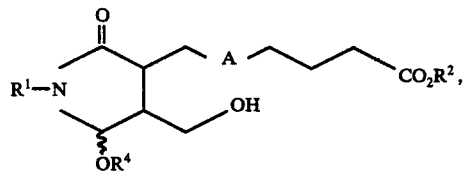

wherein $R^2$ is other than hydrogen, to form an aldehyde of the formula

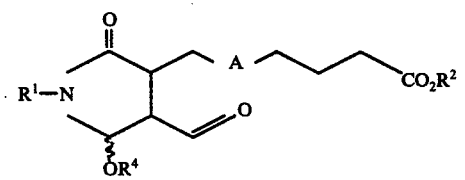

wherein $R^2$ is other than hydrogen; (b) reacting said aldehyde with a phosphonate of the formula

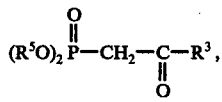

wherein $R^5$ is alkyl having 1 to 4 carbon atoms, to form a ketone of the formula

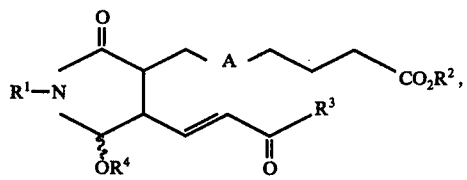

wherein $R^2$ is other than hydrogen; and then (c) reducing the keto group to an hydroxy group.

3. A pharmaceutical composition useful for inducing luteolysis or bronchospasmolysis, for inhibiting gastric juice secretion or for combatting hypertension, which composition comprises a pharmaceutical carrier and a therapeutically effective amount of a compound or salt as in claim 1.

4. The method of effecting brochodilation in a patient which comprises administering to said patient from 0.1 mg. to 10 mg. per day of a compound or salt as in claim 1.

5. The method of combatting hypertension in a patient which comprises administering to said patient from 1 mg. to 10 mg. per day of a compound or salt as in claim 1.

6. The method of inhibiting the secretion of gastric juice in a patient which comprises administering to said patient from 1 mg. to 10 mg. per day of a compound or salt as in claim 8.

7. A compound of the formula

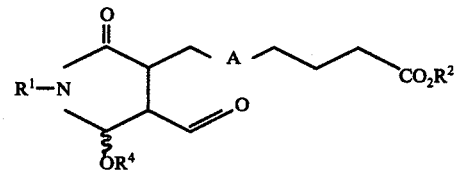

wherein $R^1$ is α-branched alkyl having 3 to 6 carbon atoms or cycloalkyl having 3 to 7 carbon atoms in the ring;

$R^2$ is lower alkyl, or cycloalkyl or aralkyl having 3 to 8 carbon atoms;

$R^4$ is alkyl having 1 to 4 carbon atoms; and

A is —C≡C—, —CH═CH—(cis), or —CH$_2$—CH$_2$—.

8. A compound of the formula

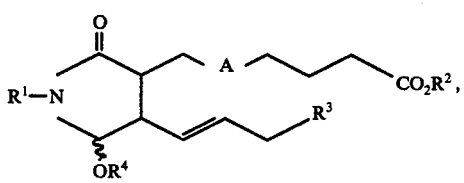

wherein $R^1$ is α-branched alkyl having 3 to 6 carbon atoms or cycloalkyl having 3 to 7 carbon atoms in the ring;

$R^2$ is lower alkyl, or cycloalkyl or aralkyl having 3 to 8 carbon items;

$R^3$ is straight-chain or branched alkyl having 1 to 10 carbon atoms, or such alkyl substituted by O-alkyl having 1 to 5 carbon atoms, by phenyl, by phenoxy, by cycloalkyl, by cycloalkyl in turn substituted by alkyl having 1 to 3 carbon atoms, or phenyl or phenoxy each in turn substituted by halogen, alkyl having 1 to 3 carbon items, or haloalkyl having 1 to 3 carbon atoms;

$R^4$ is alkyl having 1 to 4 carbon atoms; and

A is —C≡C—, —CH═CH—(cis), or —CH$_2$—CH$_2$—.

* * * * *